United States Patent [19]

Carver, Jr. et al.

[11] Patent Number: 5,316,725
[45] Date of Patent: May 31, 1994

[54] REAGENT SYSTEM FOR THE IMPROVED DETERMINATION OF WHITE BLOOD CELL SUBPOPULATIONS

[75] Inventors: Edward L. Carver, Jr., 18 Lisa Dr., Oxford, Conn. 06483; Diane D. Carver, Oxford; Mary P. Skiptunas, Naugatuck, both of Conn.

[73] Assignee: Edward Lawrence Carver, Jr., Oxford, Conn.

[21] Appl. No.: 711,965

[22] Filed: Jun. 7, 1991

[51] Int. Cl.$^5$ .............................................. G01N 1/28
[52] U.S. Cl. ...................................... 422/61; 436/17; 436/18; 252/408.1
[58] Field of Search ................ 422/61; 436/8, 10, 15, 436/17, 18, 176, 63; 252/408.1

[56] References Cited

U.S. PATENT DOCUMENTS

| | | | |
|---|---|---|---|
| 3,634,581 | 1/1972 | Thomas | 424/3 |
| 3,741,875 | 6/1973 | Ansley et al. | 435/13 |
| 4,213,876 | 7/1980 | Crews et al. | 436/18 |
| 4,286,963 | 9/1981 | Ledis et al. | 436/63 |
| 4,346,018 | 8/1982 | Carter et al. | 436/17 |
| 4,485,175 | 11/1984 | Ledis et al. | 436/63 |
| 4,521,518 | 6/1985 | Carter et al. | 436/10 |
| 4,529,705 | 7/1985 | Larsen | 436/17 |
| 4,745,071 | 5/1988 | Lapicola | 436/63 |
| 4,751,179 | 6/1988 | Ledis et al. | 435/34 |
| 4,962,038 | 10/1990 | Carter et al. | 436/10 |

FOREIGN PATENT DOCUMENTS 53-100298 1/1978 Japan.

OTHER PUBLICATIONS

Koepke et al., "A Critical Evaluation of the Manual/-Visual Differential Leukocyte Counting Method", *Blood Cells* 11:173-186 (1985).

*Primary Examiner*—James C. Housel
*Assistant Examiner*—Jeffrey R. Snay
*Attorney, Agent, or Firm*—Kramer, Brufsky & Cifelli

[57] ABSTRACT

A lytic reagent composition highly selective in its interactions with the cell membranes of white blood cells and also provides a method of using the reagent composition in a particle analyzing system to effect a significantly improved white blood cell differential determination. The lytic reagent composition is characterized by an ability to selectively shrink the white blood cells into the increasing size order of lymphocytes, basophils, monocytes, eosinophils and neutrophils, and effect a five component separation of these major subpopulations of white blood cells on the histogram of an automated blood analyzer when used in conjunction with a suitable blood diluent.

29 Claims, 6 Drawing Sheets

REAGENT SYSTEM FOR THE IMPROVED DETERMINATION OF WHITE BLOOD CELL SUBPOPULATIONS

FIELD OF INVENTION

This invention relates to an improved method and lytic reagent composition for the differentiation and enumeration of at least three subpopulations of white blood cells. When combined with a suitable blood diluent, the lytic reagent composition of the invention is characterized by an ability to consistently effect a very clean separation of white blood cells into three or more subpopulations on a leukocyte volume histogram, with little or no cellular debris. The lytic reagent composition can, in practice, enable the classification and counting of five subpopulations of white blood cells, in the order of (1) lymphocytes, (2) basophils, (3) monocytes, (4) eosinophils and (5) neutrophils. Such data are extremely useful for the detection of abnormal distributions in subpopulations of mature white blood cells and morphological abnormalities in a blood sample.

BACKGROUND OF THE INVENTION

There are three major populations of cells in the blood comprising the platelets, erythrocytes (red blood cells) and leukocytes (white blood cells). Within the white blood cell population, many subpopulations exist, five of which are considered predominantly in hematological analysis. These white cell subpopulations include monomorphonuclear lymphocytes, which constitute about 15-45% of the white blood cells in a normal mature population, polymorphonuclear basophils (0-3%); monomorphonuclear monocytes (~0-10%); polymorphonuclear eosinophils (~0-5%); and polymorphonuclear neutrophils, which constitute from about 45-80% of the mature white blood cells in a population. In many diseases, there is a clinically significant alteration in the normal distribution of these mature cell types. In addition, immature or abnormal cell types are often associated with the disease state. Hematological analysis of white blood cells, including white cell enumeration and flagging of abnormalities, in conjunction with traditional diagnostic techniques, is thus an important tool in the diagnosis and treatment of disease.

Prior to the mid-1970's, white blood cell differential analyses were conducted by manual examination, with a technician viewing blood film slides with the aid of a microscope. Since that time, hematological analysis has been automated, making its use both widespread and commonplace.

While the methodologies for automated analysis vary, most often the enumeration and analysis involves subjecting a diluted sample of whole blood to a lysing reagent which stromatolyzes and therefore eliminates the red blood cell population and simultaneously modifies the cell membranes of the more prevalent white cell subpopulations so that the cytoplasm leeches out, causing differential shrinkage of the different cell types and enabling discrimination and sorting thereof. The size and number of white blood cells in the sample are then detected with the aid of an automated analyzer, which typically includes a detector adapted to detect the volume (size) and/or opacity of the white blood cells in the sample by electrical or optical differences. The white blood cells are counted for a period of time sufficient to gather data for analysis, data points are stored in a memory device and then analyzed in an algorithmic processor. The data can then be displayed in the form of a two dimensional or three dimensional histogram.

Heretofore, a number of lysing reagents and reagent systems have been developed which have provided the clinician with the ability to isolate the white cell population from the red cell population of whole blood and to further differentiate the white cell population into smaller subpopulations. Patents considered representative of the art in the field include U.S. Pat. Nos. 4,286,963; 4,485,175; 4,529,705; 4,745,071; and WO88/07187.

U.S. Pat. No. 4,286,963 to Ledis et al describes a lytic diluent and method for achieving rapid lysis of red blood cells in whole blood. This diluent enhances the ability of automated instrumentation to perform differential determinations of lymphoid and myeloid subpopulations of leukocytes and the quantative determination of hemoglobin. The lytic diluent employed by Ledis et al is composed of a mixture of at least one quaternary ammonium salt and an aryl substituted short chain alkanol in buffered aqueous medium (pH 3.5 to 5.0). The lytic diluent of this Ledis et al patent is limited in its ability to effect differentiation of the leukocyte population into the two principal subpopulations; namely the lymphoid and myeloid fractions.

U.S. Pat. No. 4,485,175, also to Ledis et al, describes a reagent system and method for performance of differential determinations of leukocytes into three subpopulations utilizing automated cell counting equipment, in which the reagent system includes a blood diluent and lysing reagent. The lysing reagent comprises an aqueous mixture of aliphatic quaternary ammonium compounds, which when added to a diluted blood sample under mild conditions of concentration and at a relatively slow rate causes volume modifications to the various subpopulations of white blood cells, enabling a three component separation.

U.S. Pat. No. 4,529,705 to Larsen relates to a reagent for combined diluting and lysing of whole blood cells. The reagent comprises an aliphatic quaternary ammonium salt and at least one anion selected from the group consisting of sulfate, carbonate, formate and acetate anions, which are employed for the purpose of preventing aggregation of platelets in the sample and an alkali metal cyanide for conversion of hemoglobin to a chromagen.

U.S. Pat. No. 4,745,071 to Lapicola describes a reagent system for differential blood analysis including a blood diluent and lysing reagent. The lysing reagent of the '071 patent comprises an aqueous solution of a single aliphatic quaternary ammonium salt and may also contain potassium cyanide as a chromagen forming agent. The preferred quaternary ammonium salt is the dodecyl ($C_{12}$) homolog.

WO88/07187 describes a reagent system enabling differentiation of white blood cells into at least five distinct subpopulations. The PCT application discloses a reagent system comprising a lytic reagent and a companion reagent for the lytic reagent referred to as a "quench". The primary functions of the quench are to retard the activity of the lytic reagent and to restore the ionic balance of the sample subsequent to its treatment with lytic reagent.

Generally, the white blood cell differentials obtained in accordance with the described techniques fall into one of two categories. The first category is a three component screening differential resulting in the isolation and quantification of three fractions of white blood cells including a lymphocyte component, a midregion or monocyte component and a granulocyte (predominantly neutrophilic) component. The granulocyte population usually includes the neutrophils, as well as eosinophils, and possibly basophils, while the midregion often contains monocytes, other mononuclear cells, basophils and eosinophils. Separation among populations is frequently poor, resulting in low correlation between automated and manual differential counts, which is undesirable. Poor separation of subpopulations is further undesirable as it decreases the ability to accurately flag abnormalities.

The second category of white blood cell analyzers is capable of effecting a four or five component separation. Such systems are substantially more complex than the three component differential analyzers, resulting in higher costs to the operator for materials and labor. An illustration of this type of system is described in WO88/07187, a Patent Cooperation Treaty application to Coulter Electronics.

As will be appreciated by persons skilled in this area of technology, a cleaner separation between subpopulations, together with the ability to separate up to five subpopulations would result in a significant improvement in the reliability and accuracy of white blood cell differential analysis. Despite the existence of many different reagents on the market for blood differential analysis, there still exists a need for a system capable of identifying at least three and preferably five distinct subpopulations of white blood cells which is relatively simple to use and consistently effects a clean separation of the cells on a leukocyte volume histogram, to increase the ability to flag abnormalities.

Accordingly, it is an object of the present invention to provide an improved lytic reagent composition which selectively modifies blood cell volume by reacting with the cell membranes to cause red blood cells to rupture and selectively shrinks the white blood cell population into at least three distinct, highly separated components when used in combination with a suitable blood diluent.

Another object of the invention is to provide an improved lytic reagent composition capable of effecting a five component separation of white blood cells into the five major subpopulations on the leukocyte volume histogram of an automated analyzer.

A still further object of the invention is to provide a flexible blood analysis reagent system that can be optimized for both human and multiple species applications.

Yet another object of the invention is to provide an improved method for automated white blood cell differential analysis.

Further objects and advantages will be appreciated from the following disclosure.

SUMMARY OF THE INVENTION

These as well as related objects are achieved in accordance with the present invention, which provides a novel lytic reagent composition highly selective in its interactions with the cell membranes of white blood cells and also provides a method of using the reagent composition in an automated system to effect a significantly improved white blood cell differential determination. The lytic reagent composition is characterized by an ability to selectively shrink the white blood cells into the increasing size order of lymphocytes, basophils, monocytes, eosinophils and neutrophils, and effect a five component separation of these major subpopulations of white blood cells on the histogram of an automated blood analyzer when used in conjunction with a suitable blood diluent. The five component separation can be analyzed on commercially available automated blood analyzers, such as the Coulter S Plus IV blood analyzer (Coulter Electronics, Hialeah, Fla.) by manipulating the threshold values fixed within the device, optionally with the aid of image enhancement techniques, such as those described in my copending patent application U.S. Ser. No. 07/650,686, filed on Feb. 5, 1991, now U.S. Pat. No. 5,187,673. In the absence of such manipulations, the lytic reagent composition of the instant invention can readily be optimized to effect a significantly improved three component separation on the histogram of commercially available automated blood analyzers when compared to the reagents conventionally employed on such instruments.

In addition to effecting an improved white blood cell differential, the lytic reagent composition of the present invention has the advantage of being sufficiently flexible to enable optimization for differential blood analysis of multiple animal species.

The lytic reagent composition of the instant invention comprises an aqueous solution of active lytic reagents selected from the group consisting of an admixture of at least one group (A) aliphatic quaternary ammonium compound with at least one group (B) aromatic, heterocyclic or zwitterionic quaternary ammonium compound; an admixture of at least one group (A) aliphatic quaternary ammonium compound with at least one group (C) heterocyclic quaternary ammonium compound; and an admixture of at least one group (C) heterocyclic quaternary ammonium compound with at least one group (B) aromatic, heterocyclic or zwitterionic quaternary ammonium compound, wherein the group (A) quaternary ammonium compound is represented by the formula:

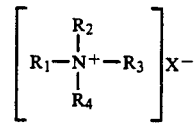

wherein $R_1$ is a long chain alkyl group containing from 10 to 20 carbon atoms, $R_2$, $R_3$ and $R_4$ are short chain alkyl groups containing from 1 to 6 carbon atoms, and X is an ion selected from the group consisting of halide, sulfate, phosphate and nitrate ions; and

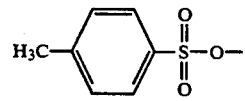

the group (B) quaternary ammonium compound is represented by the general formula:

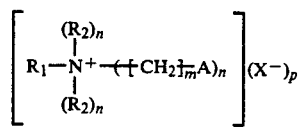

wherein $R_1$ is a long chain alkyl group comprising from 8 to 20 carbon atoms, $R_2$ is an alkyl group containing 1 to 6 carbon atoms, m is an integer from 1 to 4, A is a member selected from the group consisting of:

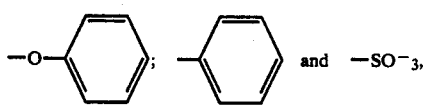

n is an integer from 0 to 1, such that when n=0, the remaining nitrogen bonds form part of a heterocyclic ring, X is an ion selected from the group consisting of halide, phosphate, sulfate and nitrate ions and p is an integer from 0 to 1.

The group (C) quaternary ammonium compound is represented by the formula

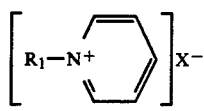

wherein $R_1$ is a long chain alkyl radical comprising from 10 to 20 carbon atoms, and X is an ion selected from the group consisting of halide, sulfate, phosphate and nitrate ions.

The use of an admixture in aqueous solution of at least one of the quaternary ammonium compounds of group (A) with at least one of the quaternary ammonium compounds of group (B), or an admixture of at least one of the quaternary ammonium compounds from group (C) with at least one of the quaternary ammonium compounds of group (B) or an admixture of at least one of the quaternary ammonium compounds from group (A) with at least one quaternary ammonium compound from group (C) in a lytic reagent composition which will selectively modify the cell membrane of white blood cells and is capable of effecting a five component separation of white blood cells into lymphocyte, basophil, monocyte, eosinophil and neutrophil subpopulations on a leukocyte histogram.

White blood cell differentiation on an automated particle analyzer in accordance with the present invention is made possible by the use of the novel lytic reagent composition of the present invention in combination with a suitable blood diluent. The blood diluent can be any of the blood diluents previously known in the art, and preferably comprises at least one organic buffer and a cell membrane stabilizing agent and an antimicrobial agent. The method of the invention comprises (1) supplying a whole blood sample, a volume of blood diluent and a volume of the lytic reagent composition to a particle analyzing system; (2) rapidly admixing in the particle analyzer the whole blood sample, the blood diluent and the lytic reagent composition of the present invention, wherein the individual quaternary ammonium compounds components in the lytic reagent composition are present in a ratio and quantity sufficient to effect at least a three component separation of white blood cells; and (3) analyzing the whole blood sample in the automated particle analyzer to differentiate and enumerate at least three subpopulations of white blood cells.

DETAILED DESCRIPTION OF THE INVENTION

Figure 1A:
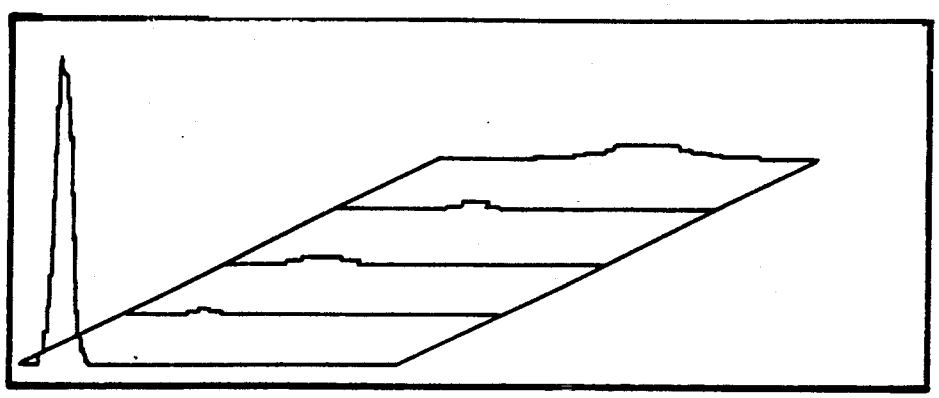
FIGS. 1A to 1C are leukocyte volumetric histograms showing the total number of cells versus cell volume for human samples, which were analyzed using the methodology and reagent system of the present invention. An image enhancement system of the type described in copending application U.S. Ser. No. 07/650,686, now U.S. Pat. No. 5,187,673 was used in the generation of the histograms. Each of FIGS. 1A to 1C shows a five component separation of white blood cells, on the increasing size order of lymphocytes, basophils, monocytes, eosinophils and neutrophils.

The reagent system of the present invention comprises a novel lytic reagent composition and a suitable blood diluent which, when combined with a sample of whole blood is capable of effectively removing the red blood cell population and consistently effecting a significantly improved separation of white blood cells on a leukocyte volume histogram of an automated blood analyzer. The reagent system has the advantage of being sufficiently flexible for optimizing automated white blood cell differentials for multiple animal species and is particularly suitable for hematological analysis of human blood samples. In the following description, the invention is first described in terms of its application in human blood analysis, after which a description of the manner in which the reagent system can be optimized for multiple species applications is provided.

The Lytic Reagent

After an extensive investigation, the inventors herein have discovered that the admixture in aqueous solution of aliphatic quaternary ammonium compounds with at least one aromatic, heterocyclic or zwitterionic quaternary ammonium detergent results in a lytic reagent that is highly selective for white blood cell membranes and is, in fact, capable of effecting a five component separation of white blood cells. During the investigation, it was also discovered that long chain alkyl pyridinium compounds in combination with at least one aliphatic quaternary ammonium compound or at least one aromatic, heterocyclic or zwitterionic quaternary ammonium compound are highly specific for white blood cell membranes and can be used to improve the separation of white blood cell subpopulations on a volumetric histogram.

The lytic reagent composition of the present invention can thus be described as an aqueous solution of active lytic reagents selected from the group consisting of:

(a) an admixture of at least one group (A) aliphatic quaternary ammonium compound with at least one group (B) aromatic, heterocyclic, or zwitterionic quaternary ammonium compound;

(b) an admixture of at least one group (A) aliphatic quaternary ammonium compound with at least one group (C) heterocyclic quaternary ammonium compound; and (c) an admixture of at least one group (C) heterocyclic quaternary ammonium compound with at least one group (B) aromatic, heterocyclic, or zwitterionic quaternary ammonium compound.

The aliphatic group (A) quaternary ammonium compound can be represented by the formula:

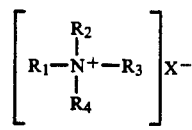

wherein $R_1$ is a long chain alkyl group containing from 10 to 20, and preferably containing 12, carbon atoms, $R_2$, $R_3$ and $R_4$ are all short chain alkyl groups containing from 1 to 6 carbon atoms, and X is an ion selected from the group consisting of halide, sulfate, phosphate, nitrate ions, and $H_3C$

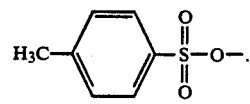

Examples of preferred group (A) aliphatic quaternary ammonium salts are described in U.S. Pat. No. 4,745,071 to Lapicola, the pertinent portions of which are incorporated by reference, with the dodecyltrimethyl ammonium halides and dodecylethyldimethyl ammonium halides being particularly preferred. Hexadecyltrimethylammonium-p-toluene sulfonate is another preferred group (A) compound.

The group (B) quaternary ammonium compound, which is either an aromatic, heterocyclic, or a zwitterionic quaternary ammonium detergent can be represented by the general formula:

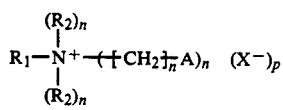

wherein $R_1$ is a long chain alkyl group containing from 8 to 20, preferably 12 to 16, carbon atoms, $R_2$ is an alkyl group containing 1 to 6 carbon atoms, m is an integer from 1 to 4, A is a member selected from the group consisting of phenyl

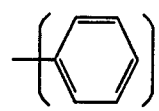

phenoxy

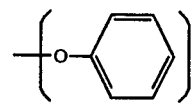

and sulfonate ($-SO^-_3$) radicals, n is an integer from 0 to 1, such that when n=0, the remaining nitrogen (N) bonds form part of a heterocyclic ring, X is an ion selected from the group consisting of halide, phosphate, sulfate, and nitrate ions and p is an integer from 0 to 1.

When the group (B) compound is a zwitterionic compound, A is preferably a sulfonate radical. Examples of the zwitterionic group (B) compounds include N-octyl-N,N-dimethyl-3-ammonio-1-propane sulfonate, N-dodecyl-N,N-dimethyl-3-ammonio-1-propane sulfonate, N-tetradecyl-N,N-dimethyl-3-ammonio-1-propane sulfonate, and N-hexadecyl-N,N-dimethyl-3-ammonio-1-propane sulfonate. Examples of the aromatic group (B) compounds include dodecyldimethyl (2-phenoxyethyl) ammonium bromide, benzyldimethyldodecyl ammonium chloride, benzyldimethyltetradecyl ammonium chloride and benzyldimethylhexadecyl ammonium chloride. In the heterocyclic compounds encompassed by the formula when n=0, the nitrogen may form part of a pyrroline ring, a pyrrolidine ring, a pyridine ring or a quinoline or isoquinoline ring. Preferably, the nitrogen forms part of a pyridine ring. A particularly preferred group (B) heterocyclic compound is hexadecyl pyridinium chloride.

The group (C) heterocyclic quaternary ammonium compound is a pyridinium compound which can be represented by the general formula:

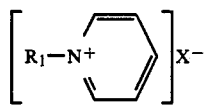

wherein $R_1$ is a long chain alkyl radical comprising from 10 to 20, and preferably 12 carbon atoms and X is an ion selected from the group consisting of halide, phosphate, nitrate and sulfate ions. Particularly preferred group (C) compounds include 1-dodecyl pyridinium chloride and hexadecyl pyridinium chloride.

The lytic reagent composition of the present invention is prepared by admixing in water (1) at least one of the group (A) compounds with at least one of the group (B) compounds; (2) at least one of the group (A) compounds with at least one of the group (C) compounds; or (3) at least one of the group (C) compounds with at least one of the group (B) compounds. Preferably the water is deionized.

In order to achieve optimum separation between subpopulations of white blood cells, it is important that the ratio of the individual quaternary ammonium compound components of the lytic reagent composition be controlled. In accordance with the invention, it has been determined that optimum separation can ordinarily be achieved when the ratio of the group (A) compound to the group (B) compound in the lytic reagent composition ranges from about 5:1 to about 75:1; the ratio of the group (A) compound to group (C) compound ranges from about 0.01:1 to about 99:1, and the ratio of the group (C) compound to group (B) compound ranges from about 5:1 to 75:1, respectively.

The optimum ratio of the individual components of the active lytic reagents may vary, depending upon, for example, the chemical activity of the compounds selected and the individual instrument to be utilized in the differential analysis. optimization of the ratio within the ranges provided is considered well within the skill in the art and can be achieved, for example, by varying the relative amounts of the individual quaternary ammonium compound components in the lytic reagent composition, conducting an analysis on the particular analyzer to be used and conducting an ocular trauma test to determine the ratio which effects the cleanest separation on the leukocyte histogram.

The total concentration of the active lytic ingredients in the lytic reagent composition will typically be from about 7 to about 370 gms/liter. It should be understood, however, that the concentration of the active lytic reagents in the composition can be altered if the volume of the lytic reagent composition is modified accordingly, as long as the ratio of the individual quaternary ammonium compound is maintained within the defined limits.

To form a suitable chromagen for hemoglobin determination, as is desired for operation of most of the commercially available automated blood analyzers, the lytic reagent composition of the present invention can also be provided with an alkali metal cyanide, such as potassium cyanide (KCN). Other chromagen forming agents can also be employed. It should be appreciated, however, that the alkali metal cyanide is an optional ingredient used to accomplish a hemoglobin determination and is not critical for achieving a three or a five component separation of white blood cells on a leukocyte volume histogram.

A particularly preferred formulation for the lytic reagent composition is:

| Ingredient | Preferred Concentration |
|---|---|
| (B) benzyldimethyl tetradecyl ammonium chloride | 6.5 gm/liter |
| (C) 1-dodecyl pyridinium chloride | 89.5 gm/liter |
| KCN | 0.75 gm/liter |
| water | sufficient for 1 liter |

The Blood Diluent

The lytic reagent composition of the present invention is used in combination with a suitable blood diluent. The diluent can be essentially any one of the diluents heretofore used in blood differential analysis. Preferably, the diluent is an isotonic composition comprising at least one organic buffer, a cell membrane stabilizing means and an antimicrobial agent. Most preferably, the diluent is an isotonic composition comprising at least one organic buffer and a monoaldehyde as the cell membrane stabilizing means and antimicrobial agent. Alternatively, a germicidal, such as 1-hydroxypyridine-2-thione, which will not adversely interfere with the ionic strength, osmolality, pH, or other cell volume determining characteristics, or red or white blood cell lysing characteristics of the lytic reagent, can be employed.

The organic buffers which can be used in the blood diluent include ADA (N-[2-Acetamido]-2-iminodiacetic acid; N-[Carbamoylmethyl]iminodiacetic acid), MOPS (3-[N-Morpholino]propanesulfonic acid), PIPES (Piperazine-N,N'-bis[2-ethanesulfonic acid]; 1,4-Piperazinediethanesulfonic acid), HEPES (N-[2-Hydroxyethyl]piperazine-N'-[2-ethanesulfonic acid]), BES [N,N-bis[2-Hydroxyethyl]-2-aminoethanesulfonic acid; 2-[bis(2-Hydroxyethyl)amino]ethanesulfonic acid) BIS-TRIS (bis[2-Hydroxyethyl)imino tris-[hydroxymethyl]methane; 2-bis[2-Hydroxyethyl]-amino-2-[hydroxymethyl]-1,3-propanediol); TES (N-tris[Hydroxymethyl]methyl-2-aminoethanesulfonic acid; 2-([2-Hydroxy-1,1-bis(hydroxymethyl)-ethyl]amino)ethanesulfonic acid), TAPSO (3-[N-tris(Hydroxymethyl)methylamino]-2-hydroxypropanesulfonic acid), MES (2-[N-Morpholino]ethanesulfonic acid), DIPSO (3-[N,N-bis(2-Hydroxyethyl)amino]-2-hydroxypropanesulfonic acid), MOPSO (3-[N-Morpholino]-2-hydroxypropanesulfonic acid), TRIS (tris[hydroxymethyl]aminomethane), and ACES (2-[2-Amino-2-oxoethyl)-amino]ethanesulfonic acid; N-[2-Acetamido]-2-aminoethanesulfonic acid). ACES is particularly preferred.

In addition to diluting the blood sample for enumeration, the purpose of the diluent system is to suitably stabilize cell size, shape and integrity of all of the blood cellular components both before and after treatment with the lytic reagent composition, in order to promote the diagnostic accuracy of blood histograms derived from automated volume analysis and distribution. To accomplish this purpose, a preferred formulation of the isotonic diluent is:

| Ingredient | Effective Conc. Range | Most Preferred |
|---|---|---|
| sodium sulfate | 7.5–12.5 | 9.7 gm/liter |
| sodium chloride | 3.0–5.0 | 4.0 gm/liter |
| organic buffer | 0.1–4.0 | 2.0 gm/liter |
| formaldehyde | 0.1–1.5 | 1.0 ml/liter |
| water | | sufficient for one liter |

The advantages of this diluent are described in my copending patent application filed simultaneously herewith.

The pH of the diluent should be adjusted to about 7.1±1.4, and diluent osmolality adjusted to about 325±50 milliosmoles with sodium chloride.

The described diluent will produce accurate histograms with virtually any of the automated or semiautomated blood analyzers but will produce significantly improved three component and five component histograms when used in conjunction with the lytic reagent composition of the present invention.

The Method

In accordance with the inventive methodology, a whole blood sample, a volume of diluent and a volume of the lytic reagent composition are supplied to an automated analyzer and rapidly admixed therein, such that the ratio of the individual quaternary ammonium components in the lytic reagent composition are present in a ratio and quantity sufficient to effect at least a three component separation of white blood cells and then using the automated analyzer to differentiate and quantify at least one of the white blood cell subpopulations.

In a preferred embodiment, the lytic reagent composition is first admixed with an initial volume of diluent. The whole blood sample is then dispensed into the thus prepared lyse/diluent mixture, with a second volume of diluent. In accordance with this embodiment, the initial volume of diluent can be varied in order to adjust the lytic strength of the reagent composition, while the final volume of diluent can be varied in order to adjust the final dilution ratio.

The final ratio of blood diluent to lytic reagent composition will typically be from about 5:1 to about 250:1 and the final dilution of the blood will be from about 5 to 1000, generally about 250 parts by volume total diluent and lytic reagent composition per part by volume of the whole blood sample. The quantity of total active lytic reagents to the volume of blood in the counting cuvette of the analyzer should range from about 0.15 mg total active lytic reagents/$\mu$l whole blood to about 3.2 mg total active lytic reagents/$\mu$l whole blood.

The pH of the final dilution should be from about 5.25 to about 8.75. When the pH of the final dilution is below 5.25, the neutrophils will shrink faster than the lymphocytes and all subpopulations will begin to merge, which is highly undesirable. If the pH exceeds about 8.75, the lymphocytes will fail to shrink properly and will remain too large in relation to the neutrophils, again causing a merger effect.

It should be appreciated that the above values are only examples based upon successful formulations and reasonable deviations therefrom also will provide useful results in achieving the objects of the invention.

In the automated analyzer, the whole blood/reagent system mixture remains in the lysing chamber for a short but sufficient amount of time for the red blood cells to be stromatolyzed and release their hemoglobin and for the active lytic reagents to act on the cell membranes of the white blood cells and cause them to shrink. As will be readily appreciated by persons skilled in this area of technology, the incubation times may vary depending on factors such as the strength of the active lytic reagents used in the lytic reagent composition and the total final concentration of the active lytic reagent in the sample. As a general guideline, for human blood analysis, the whole blood/reagent system mixture will generally remain in the lysing chamber for a period of time ranging from about 10 to about 30 seconds. The determination of the precise incubation time for a given reagent system in accordance with the present invention can be readily accomplished by persons skilled in the art.

The suspension resulting from the foregoing is then passed through sensing apertures in a leukocyte counting bath, wherein the white blood cells are counted and the volume (size) and/or opacity is measured by electrical or optical differences. There, the white blood cells are counted for a period of time to gather sufficient data for analysis, typically about 10,000 cells. The data points are stored and analyzed in a histogrammer, and visually displayed on a white blood cell histogram such as the one illustrated in FIG. 1.

Using an automated blood differential analyzer, including an image enhancement system described in copending U.S. patent application Ser. No. 07/650,686, the inventors herein have discovered that the lytic reagent compositions described herein are highly selective for the membranes of the various white blood cell subpopulations and are surprisingly capable of effecting a volume separation of the white blood cells into five subpopulations. After treatment with the reagent system, the volumes of the lymphocytes, basophils, monocytes, eosinophils and neutrophils in the human white blood cell population were found to be in the vicinity of 40–109, 110–124, 125–165, 166–200, and 201–500 femtoliters, respectively.

Although the lytic reagent compositions of the present invention are capable of effecting a five component separation of white blood cells, the five components cannot automatically be readily visualized from the histograms plotted by commercially available automated differential analyzers. A five component fractionation can, however, be analyzed on such systems by manipulating the threshold values set within the instruments themselves in accordance with the volume information and peak locations provided herein. Such manipulations are within the skill in the art and will be readily appreciated by the manufacturers of automated and semiautomated differential analyzers.

When utilized on commercially available differential analyzers in the absence of any threshold manipulations, the lytic reagent compositions of the present invention are capable of showing an improved three component separation of white blood cells when compared to the reagent systems typically employed on such analyzers. This aspect of the invention is illustrated in Example 3 herein, wherein exemplary lytic reagent compositions within the scope of the present invention were comparatively tested on commercial differential analyzers of several of the leading instrument manufacturers.

In order to optimize for an improved three component separation on other manufacturers' instruments, it is necessary to determine the optimum ratio of the individual quaternary ammonium compound components as well as the total concentration of active lytic reagents in the lysing composition. The inventors herein have found that the preferred method of optimization involves the utilization of a full factorial experimental design in accordance with the methodology described by Box et al, *Statistics For Experimentors*, John Wiley & Sons, publishers (1978) (the pertinent portions of which are hereby incorporated by reference) in combination with a visual comparison of the resulting histograms. The use of experimental design is employed to reduce the number of tests required to determine the optimum ratio and total concentration of the active lytic reagents for a given instrument. Since most commercial analyzers are fixed in terms of diluent volumes, blood volume, end point dilution ratios, and incubation time, the only variables to be optimized for any given instrument are the ratio of individual quaternary ammonium compound components and total quantity of the active lytic reagents.

Multispecies Applications

A particular advantage of the present invention is that the reagent system and methodology can be adapted for multispecies applications. Since, however, the physiology of white blood cell membranes can differ significantly from species to species, the reagent system must be optimized for each animal species whose blood is to be analyzed. Optimization is best effected utilizing the full factorial experimental design in accordance with the methodology of Box et al, cited hereinabove.

Parameters to be optimized include the ratio of the individual quaternary ammonium compound components in the lytic reagent composition, the total amount of the active lytic reagents per unit volume of whole blood, the strength of the lytic reagent composition and the incubation time prior to enumeration.

The full factorial design methodology as utilized by the inventors herein is illustrated in Example 4 herein. Using this methodology, the inventors have optimized a number of different lytic reagent compositions for several animal species, including the canine and feline species. Optimized values for a lytic reagent composition comprising 1-dodecylpyridinium chloride (group C) and benzyldimethyltetradecyl ammonium chloride (group B) are provided in Table 1 below.

TABLE 1

| Species | Ratio Lytic Agents | Ratio Lytic Agent: Blood Sample | Ratio Lyse: Diluent | Time (Seconds) |
|---|---|---|---|---|
| Canine | 37.1:1 | 0.58:1 | 1:24.5 | 20 |
| Feline | 12:1 | 0.38:1 | 1:16.9 | 10 |

Using the aforementioned full factorial design methodology, the reagent system of the present invention can be optimized for virtually any species of animal.

The present invention will be more clearly understood from the following specific examples. These examples are for illustrative purposes and are not to be construed as limiting the spirit and scope of the invention in any way.

EXAMPLE 1

This example illustrates the preparation of a preferred lytic reagent composition of the present invention and the use of the lytic reagent composition in an automated differential analyzer to effect a five component separation of white blood cells from a sample of human whole blood.

An example of a preferred lytic reagent composition in accordance with the invention was formulated in accordance with the following:

| Component | Amount per liter |
|---|---|
| 1-dodecyl pyridinium chloride (Group C) | 89.5 grams |
| benzyldimethyl tetradecyl ammonium chloride (Group B) | 6.5 grams |
| water | sufficient to make one liter |

This lytic reagent composition is suitable for use with diluted blood samples. In this example the blood diluent had the following formulation:

| Component | Amount per liter |
|---|---|
| sodium sulfate | 9.7 gm/liter |
| sodium chloride | 4.0 gm/liter |
| organic buffer | 2.0 gm/liter |
| formaldehyde | 1.0 ml/liter |
| water | sufficient for one liter |

A 140 $\mu$l sample of the lytic reagent composition was rapidly dispensed into the counting cuvette of the automated analyzer with 2.0 ml. of the blood diluent (the initial diluent) using a precise metering device, i.e., a syringe. 20 $\mu$l of whole blood sample was partitioned off using a pipetting tip and rapidly dispensed into the counting cuvette with 2.84 ml of the blood diluent (final diluent) using a syringe, to obtain a total diluent volume of 4.84 ml and a final total volume in the counting cuvette of 5.0 ml. The reagents were dispensed at a rate and in such a fashion to accomplish a rapid and thorough mixing of the sample.

The diluted sample was analyzed for leukocyte volume and enumeration by electronic resistance measurements of the sample passing through an orifice. Scanning was conducted for 10 seconds after addition of the reagent system. An image enhancement apparatus of the type described in copending application U.S. Ser. No. 07/650,686, now U.S. Pat. No. 5,187,673, was utilized in order to enhance the visualization of the separation effected using the reagent system of the invention.

Figure 1B:
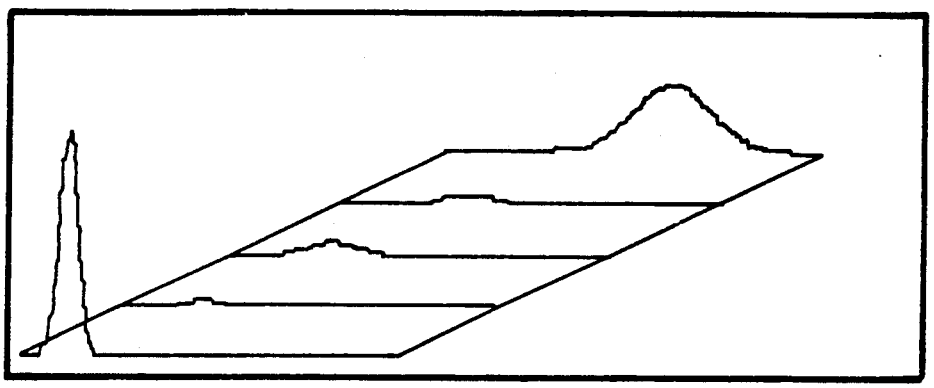
Figure 1C:
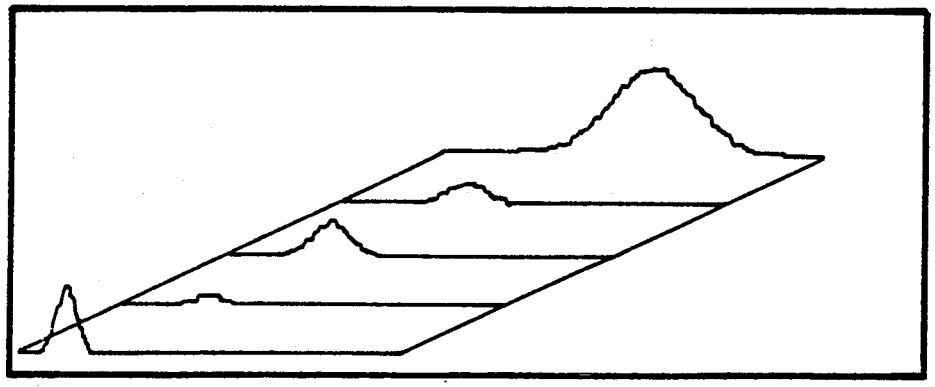

Three different blood samples, designated samples 1, 2 and 3 were analyzed in accordance with the foregoing. The resulting histograms are reproduced in FIGS. 1A–1C, respectively. As illustrated in FIGS. 1A–1C, the reagent system of the present invention effected a five component separation of the five major subpopulations of white blood cells on the increasing size order of lymphocytes, basophils, monocytes, eosinophils and neutrophils, respectively.

The counts obtained on the automated analyzer for each of samples 1, 2 and 3 were then compared to manual counts obtained for each of three samples, the results of which are set forth below.

|  | lymphocytes | basophils | monocytes | eosinophils | neutrophils |
|---|---|---|---|---|---|
| SAMPLE 1 | | | | | |
| Manual Count | 77 | — | 3.4 | 1.8 | 17.8 |
| Analyzer | 71 | 1.4 | 2.7 | 3.3 | 21.6 |
| SAMPLE 2 | | | | | |
| Manual Count | 37 | 1 | 4.2 | 3.2 | 54.6 |
| Analyzer | 38.8 | 1.3 | 5.6 | 3.7 | 50.6 |
| SAMPLE 3 | | | | | |
| Manual Count | 9.8 | 0.5 | 11 | 6.9 | 71.8 |
| Analyzer | 11.7 | 1.4 | 10.9 | 7.9 | 68.1 |

As can be appreciated by a skilled clinician or diagnostitian, these results display strong correlation not only for the normal sample but also for the two highly abnormal samples. Additional information including correlation coefficients and flagging rates is discussed in Example 2.

EXAMPLE 2

Approximately 220 human blood samples were analyzed using the reagent system and method described in Example 1. Correlation coefficients with manual microscopic examination and flagging rates were determined in accordance with the NCCLS standard for Reference Leukocyte Differential Count And Evaluation Of Instrumental Methods. The average results are summarized in Tables 2 and 3 below.

TABLE 2

| Correlation Coefficients | | | | |
|---|---|---|---|---|
| lymphocytes | basophils | monocytes | eosinophils | neutrophils |
| 0.98 | 0.18 | 0.55 | 0.48 | 0.95 |

TABLE 3

| Flagging Rates | | |
|---|---|---|
| | Instrument Negative | Instrument Positive |
| Reference Normal | True Negative 84.2% | False Positive 15.8% |
| Reference Abnormal | False Negative 4.2% | True Positive 95.8% |

These preliminary data on more than 200 normal and abnormal blood specimens indicate a high degree of correlation between leukocyte population data from the prototype analyzer and the manual 800 cell differentials. Lower correlation coefficients for basophils, monocytes and eosinophils are common because the leukocyte population data from the prototype analyzer and the manual 800 cell differentials. Lower correlation coefficients for basophils, monocytes and eosinophils are common because the range of sample variation is narrow.

The flagging rates indicate a high efficiency rate and the ability of the system to flag abnormal samples 95.8 percent of the time without causing excessive flagging of normal samples.

The typical variation from technician to technician when comparing the manual reference method to itself is reported by Koepke, J. et al, "A Critical Evaluation of The Manual/Visual Differential Leukocyte Counting Method", Blood Cells (1985) 11:173–186.

EXAMPLE 3

This example illustrates that the lytic reagent system of the present invention, when used in combination with a suitable blood diluent, is capable of effecting an improved three component separation of white blood cells on commercially available automated particle analyzers when compared to the reagent systems conventionally employed on such analyzers.

In each of the experiments herein, the automated analyzers were run in accordance with the manufacturer's instructions, using either the reagent system of the present invention or the reagent system recommended by the respective manufacturers and routinely employed in the automated analyzers.[1] All other parameters were maintained constant.

| | | |
|---|---|---|
| 1. dodecylethyldimethyl ammonium bromide | 27.6 | gm |
| N-dodecyl-N,N-dimethyl-3 ammino 1-propane sulfonate | 2.76 | gm |
| KCN | 0.25 | gm |
| water | 1000 | ml |
| 2. dodecylethyldimethyl ammonium bromide | 27.6 | gm |
| benzyldimethyltetradecyl ammonium chloride | 0.792 | gm |
| KCN | 0.25 | gm |
| water | 1000 | ml |
| 3. dodecyltrimethyl ammonium chloride | 27.0 | gm |
| dodecyldimethyl (2-phenoxy ethyl) ammonium bromide | 3.86 | gm |
| KCN | 0.25 | gm |
| water | 1000 | ml |

Experiment 1

In this experiment, whole blood samples were analyzed on a CELL-DYN® 1600 automated blood analyzer available from Unipath. The following lytic reagent compositions were prepared and loaded onto the CELL-DYN® 1600 automated analyzer. The diluent was the same as that described in Example 1.

Figure 2A:
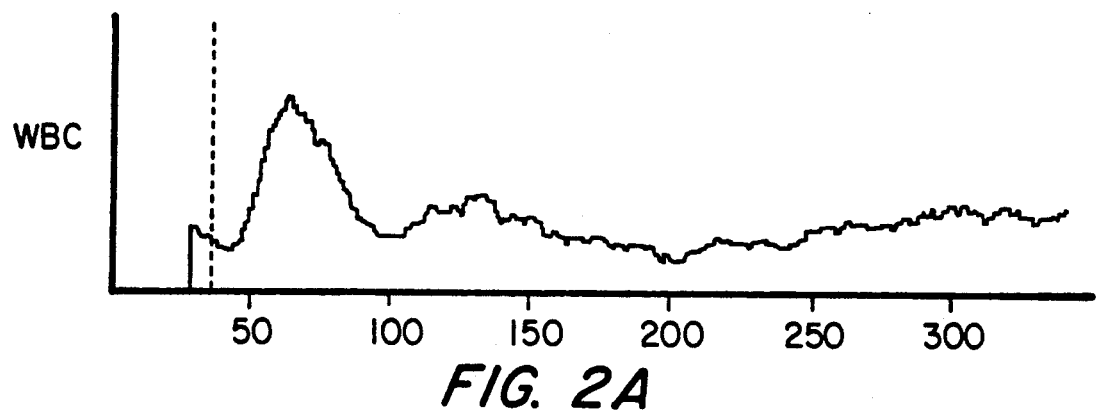
FIG. 2A is a leukocyte volume histogram obtained in accordance with the present invention, in Example 3, Experiment 1 herein, on a Unipath CELL-DYN ® 1600 automated analyzer wherein the lytic reagent was lytic reagent 1 comprising dodecylethyldimethyl ammonium bromide and N-dodecyl-N,N-dimethyl-3 ammonia 1-propane sulfonate and the whole blood sample was blood sample A.
Figure 2B:
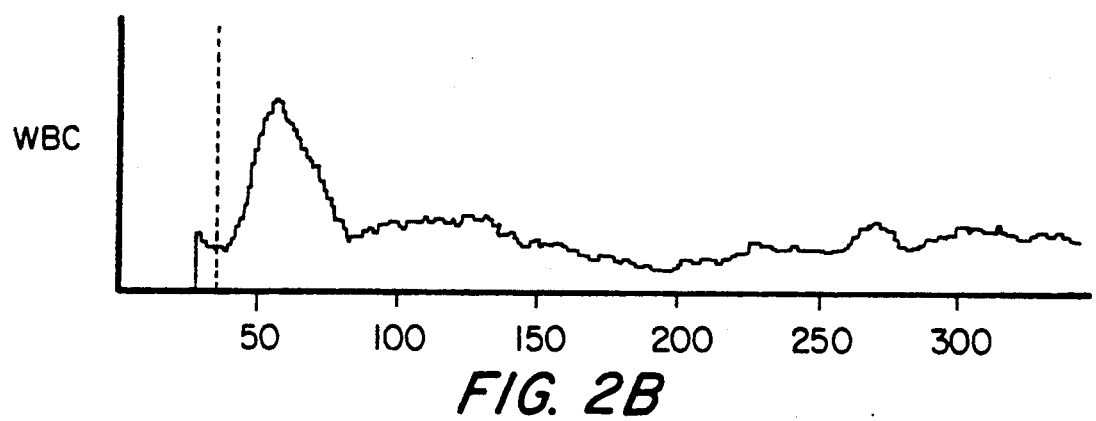
FIG. 2B is a leukocyte volume histogram obtained in accordance with the present invention, on a Unipath CELL-DYN ® 1600 automated analyzer in Example 3, Experiment 1, wherein the lytic reagent was lytic reagent composition 2, comprising dodecylethyldimethyl ammonium bromide and benzyldimethyltetradecyl ammonium chloride and the whole blood sample was blood sample A.
Figure 2C:
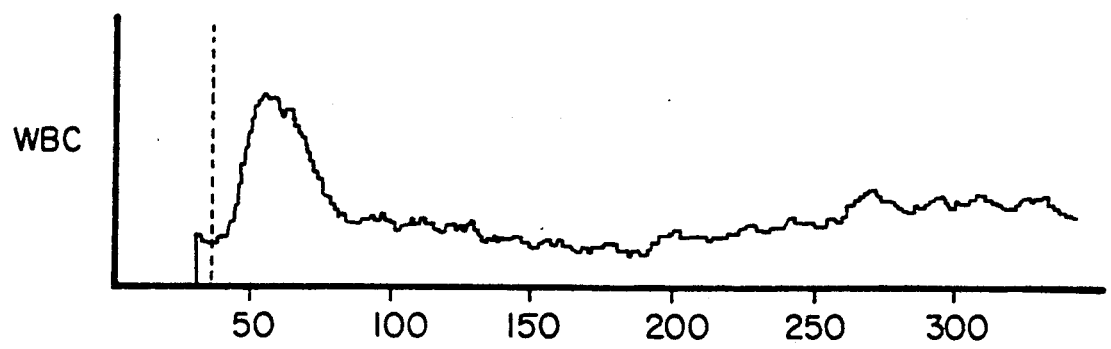
FIG. 2C is a comparative leukocyte volume histogram obtained for whole blood sample A on a Unipath CELL-DYN ® 1600 automated analyzer using the manufacturer's recommended reagent system.
Figure 2D:
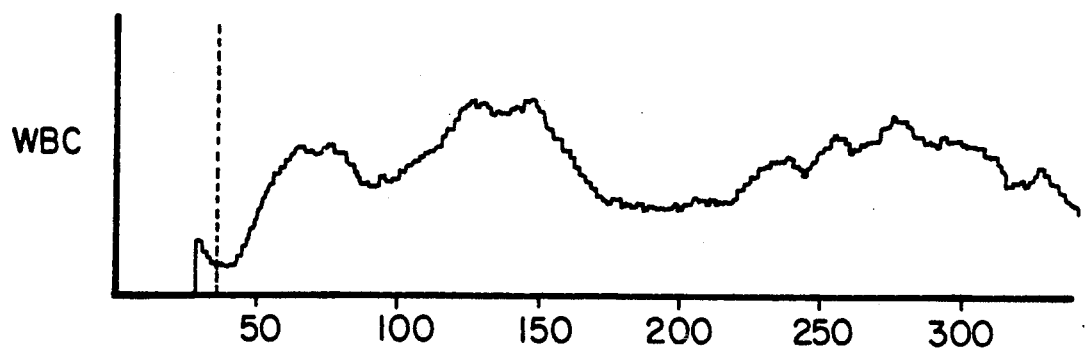
FIG. 2D is a leukocyte volume histogram obtained in accordance with the present invention in Example 3 on a Unipath CELL-DYN ® 1600 automated analyzer, Experiment 1 herein, wherein the lytic reagent was lytic reagent 1 and the whole blood sample was blood sample B.
Figure 2E:
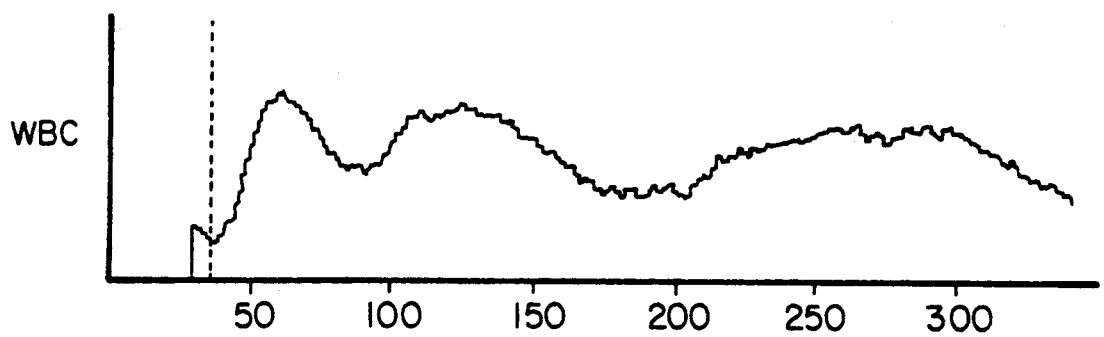
FIG. 2E is a leukocyte volume histogram obtained in accordance with the present invention on a Unipath CELL-DYN ® 1600 automated analyzer in Example 3, Experiment 1, wherein the lytic reagent was lytic reagent composition 2 and the whole blood sample was blood sample B.
Figure 2F:
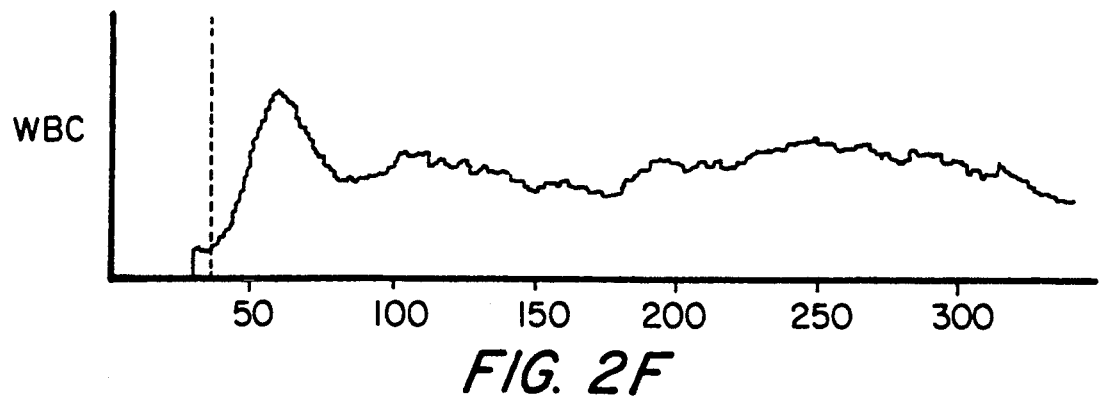
FIG. 2F is a comparative leukocyte volume histogram obtained for whole blood sample B on a Unipath CELL-DYN ® 1600 automated analyzer using the manufacturer's recommended reagent system.
Figure 2G:
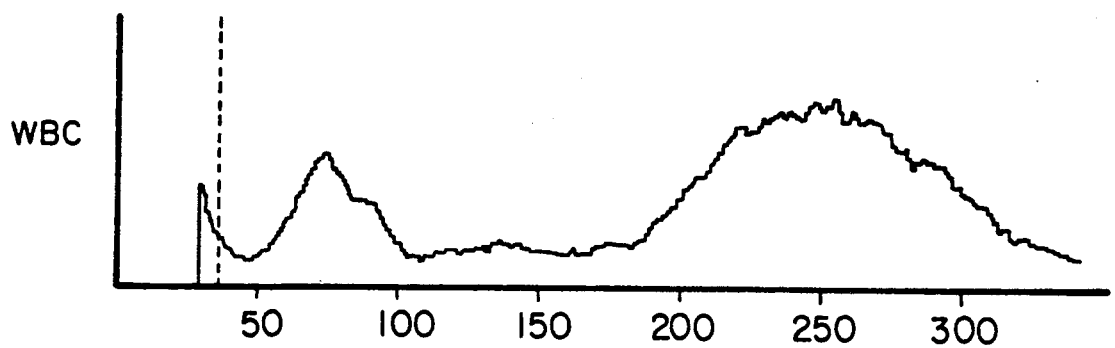
FIG. 2G is a leukocyte volume histogram obtained in accordance with the present invention, in Example 3, Experiment 1 herein on a Unipath CELL-DYN ® 1600 automated analyzer, wherein the lytic reagent was lytic reagent composition 3 comprising dodecyltrimethyl ammonium chloride dodecyldimethyl (2-phenoxy ethyl) ammonium bromide and the whole blood sample was blood sample C.
Figure 2H:
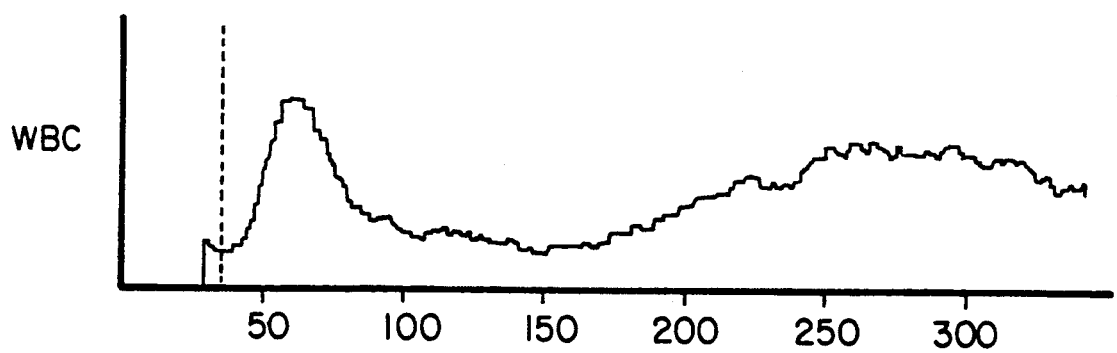
FIG. 2H is a comparative leukocyte volume histogram obtained for whole blood sample C on a Unipath CELL-DYN ® 1600 automated analyzer using the manufacturer's recommended reagent system.
Figure 3A:
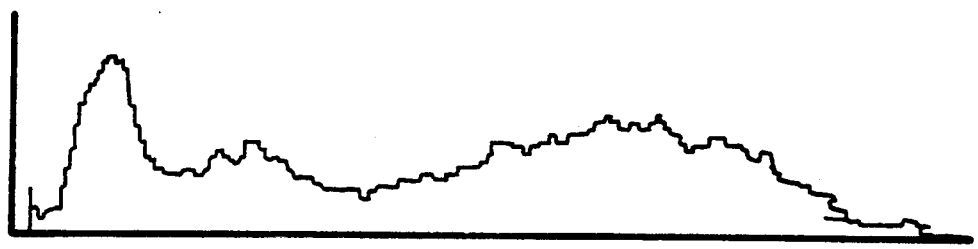
FIG. 3A is a leukocyte volume histogram showing the total number of cells versus cell volume for the human blood sample analyzed in Example 3, Experiment 2 herein, using a lytic reagent composition of the present invention comprising 1-dodecylpyridinium chloride and benzyldimethyltetradecyl ammonium chloride in a Coulter S Plus II ® automated particle analyzer (Coulter Electronics, Hialeah, Fla.).
Figure 3B:
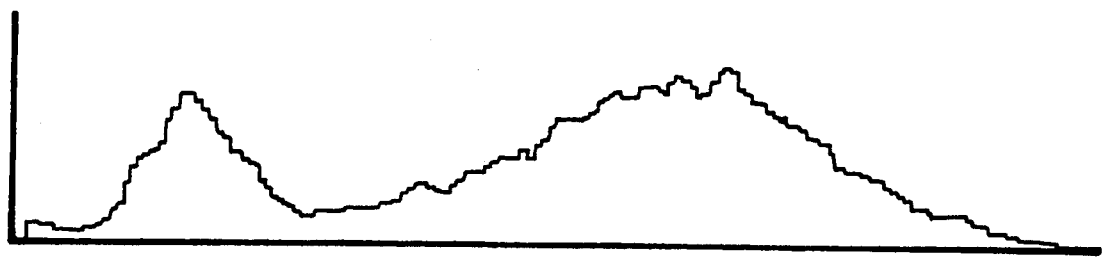
FIG. 3B is a comparative histogram showing total number of cells versus cell volume for the same human blood sample analyzed in Example 3, Experiment 2, which was analyzed on the COULTER S PLUS II ® automated analyzer using the blood differential reagent system recommended by the manufacturer.

Each of the foregoing lytic reagent compositions (1, 2 and 3, respectively) was run on the CELL-DYN 1600 automated analyzer in combination with the specified blood diluent and whole blood samples A, B and C. The resulting histograms are set forth in FIGS. 2A, 2B, 2D 2E and 2G. For comparison, the same blood samples were then also run on the automated instrument using the reagent system recommended by the manufacturer. The resulting comparative histograms are reproduced as FIGS. 2C, 2F and 2H respectively. As is apparent from a comparison of FIGS. 2A and 2B with FIG. 2C, FIGS. 2D and 2E with FIG. 2F, and FIG. 2G with FIG. 2H, in each instance a cleaner separation was effected utilizing the reagent system, including the lytic reagent composition, of the present invention.

Experiment 2

In this experiment, a sample of whole blood was analyzed on a COULTER S PLUS II automated analyzer (Coulter Electronics, Inc., Hialeah, Fla.), using first a reagent system, including a lytic reagent composition of the present invention, and then using the lyse/diluent combination recommended by Coulter Electronics for use in the COULTER S PLUS II analyzer, as described in U.S. Pat. No. 4,521,518. The lytic reagent composition of the present invention utilized in this experiment was comprised of an admixture of 46.0 grams of 1-dodecylpyridinium chloride, 3.3 grams of benzyldimethyl tetradecyl ammonium chloride and 0.6 grams KCN as a chromagen-forming reagent in 1000 ml of water. The diluent was the same as in Example 2.

The COULTER S PLUS II analyzer does not effect any special mixing procedure, such as that described in U.S. Pat. No. 4,485,175, yet by comparing the resulting histograms, it is apparent that the reagent of the present invention is capable of effecting a separation of three populations of white blood cells while the manufacturer's reagents on the same analyzer separated only two populations of cells.

Experiment 3

In this experiment, a sample of whole blood was analyzed on a COULTER S PLUS IV automated analyzer (Coulter Electronics, Inc., Hialeah, Fla.), using first a reagent system, including a lytic reagent composition of the present invention, and then using the lyse/diluent combination recommended by Coulter Electronics for use in the COULTER S PLUS IV analyzer, as described in U.S. Pat. No. 4,485,175. The lytic reagent composition of the present invention utilized in this experiment was comprised of an admixture of 19.2 grams of dodecylethyldimethyl ammonium chloride, 1.5 grams of hexadecyl pyridinium chloride and 0.6 grams KCN as a chromagen-forming reagent in 1000 ml of water. The diluent was the same as in Example 2.

Figure 4A:
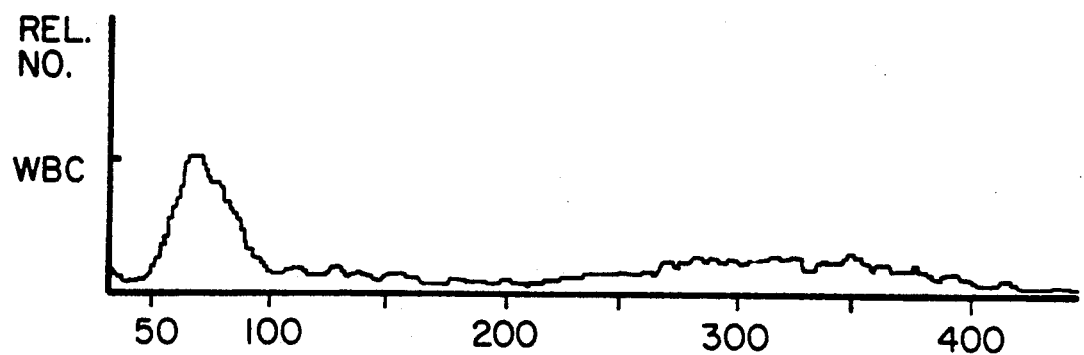
FIG. 4A is a leukocyte volume histogram showing the total number of cells versus cell volume for the human blood sample analyzed in Example 3, Experiment 3 herein, using a lytic reagent composition of the present invention comprising dodecylethyldimethyl ammonium chloride and hexadecylpyridinium chloride in a COULTER S PLUS IV ® automated differential particle analyzer.
Figure 4B:
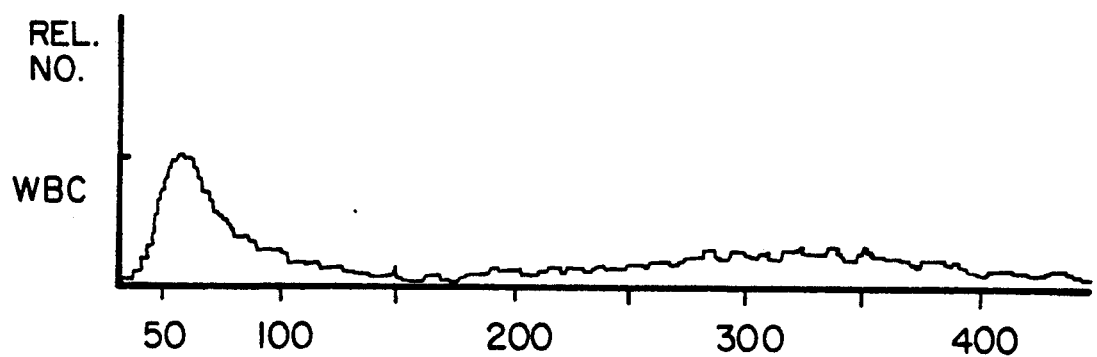
FIG. 4B is a comparative leukocyte volume histogram showing total number of cells versus cell volume for the same human blood sample illustrated in FIG. 4A, which was analyzed on the Coulter S Plus IV ® automated particle analyzer using the blood differential reagent system recommended by the manufacturer.

The resulting histograms are set forth in FIGS. 4A and 4B, with FIG. 4A illustrating the histogram obtained from the analysis employing the reagent system of the present invention.

As can be seen by a comparison of the histograms obtained in accordance with the present invention, versus those obtained utilizing the reagent systems currently available on the market and recommended for use in the commercially available automated analyzers, the lytic reagent compositions of the present invention, when combined with a suitable blood diluent, yield cleaner three component separations of white blood cells.

EXAMPLE 4

This example illustrates the use of full factorial experimental design for optimization of the reagent system of the present invention for multiple species of animals. The experimental design is employed in order to reduce the number of tests necessary for optimization of the critical parameters for a given species.

In accordance with this procedure, stock solutions of the lytic reagents are prepared in known concentrations and starting lyse volume, blood sample volume and total fluid volume are set. For example, for optimization of the reagent system including a group (A) aliphatic quaternary ammonium compound and a group (B) aromatic, heterocyclic or zwitterionic quaternary ammonium compound for the feline species, the following values could be set:

| | |
|---|---|
| Group (A) aliphatic quaternary (stock solution) | 140 gm/liter |
| Group (B) aromatic, heterocyclic or zwitterionic quaternary ammonium compound (stock solution) | 10 gm/liter |
| Starting lyse volume | 140 μl |
| Blood sample volume | 20 μl |
| Total fluid volume | 5 ml | in which the lyse (A)(μl), lyse (B)(μl), blood (μl), initial diluent (ml) and final diluent (ml) equals the total fluid volume, in this case 5 ml.

A starting matrix is then prepared, wherein the volume of the lytic reagent stock solutions, initial diluent volume and incubation time range from low to high. An example of the starting matrix is set forth below.

TABLE 1

| Quantity | Volume Group (A) stock solu. | Volume Group (B) stock solu. | Initial Diluent | Incubation Time (seconds) |
|---|---|---|---|---|
| Low | 10% | 10% | .5 ml | 10 |
| Medium | 50% | 50% | 2.5 ml | 20 |
| High | 90% | 90% | 4.5 ml | 30 |

The matrix is then run, varying the highs, medium and lows, to arrive at a series of experiments which will all then be run on an automated particle analyzer using the same blood sample. An optical trauma test or visual inspection of the resulting histograms is then conducted, and the best results selected. The best values then become the midpoints of the next series of tests.

An example of a full factorial design matrix is set forth below.

TABLE 2

| | Full Factorial Design | | | |
|---|---|---|---|---|
| Run # | Volume Group (A) stock | Volume Group (B) stock | Initial Diluent | Time (seconds) |
| 12 | high | high | low | high |
| 17 | mid | mid | mid | mid |
| 3 | low | high | low | low |
| 5 | low | low | high | low |
| 20 | mid | mid | mid | mid |
| 10 | high | low | low | high |
| 8 | high | high | high | low |
| 9 | low | low | low | high |
| 16 | high | high | high | high |
| 2 | high | low | low | low |
| 19 | mid | mid | mid | mid |
| 4 | high | high | low | low |
| 18 | mid | mid | mid | mid |
| 13 | low | low | high | high |
| 6 | high | low | high | low |
| 1 | low | low | low | low |
| 15 | low | high | high | high |
| 11 | low | high | low | high |
| 7 | low | high | high | low |
| 14 | high | low | high | high |

For the foregoing experiments, the blood sample volume is fixed at 20 μl of blood and the total volume is 5.0 ml.

The actual values for several of the runs to be conducted in accordance with the Table 2 matrix are set forth in Table 3 below.

TABLE 3

| | Group A stock solution | Group B stock solution | Initial Diluent | Blood Sample | Time (seconds) | Final Diluent |
|---|---|---|---|---|---|---|
| L | 14 μl | 14 μl | 0.5 ml | 20 μl | 10 | 4.452 ml |

TABLE 3-continued

| | Group A stock solution | Group B stock solution | Initial Diluent | Blood Sample | Time (seconds) | Final Diluent |
|---|---|---|---|---|---|---|
| (10%) | (1.96 mg) | (0.14 mg) | | | | |
| M | 70 μl | 70 μl | 2.5 ml | 20 μl | 20 | 2.34 ml |
| (50%) | (9.8 mg) | (0.7 mg) | | | | |
| H | 126 μl | 126 μl | 4.5 ml | 20 μl | 30 | 0.228 ml |
| (90%) | (17.64 mg) | (1.26 mg) | | | | |
| RUN # | | | | | | |
| 12 | High 126 μl (17.64 mg) | High 126 μl (1.26 mg) | Low 0.5 ml | 20 μl | High 30 | 4.228 ml |
| 17 | Mid 70 μl (9.8 mg) | Mid 70 μl (0.7 mg) | Mid 2.5 ml | 20 μl | Mid 20 | 2.34 ml |
| 3 | Low 14 μl (1.96 mg) | High 126 μl (1.26 mg) | Low 0.5 ml | 20 μl | Low 10 | 4.34 ml |
| 5 | Low 14 μl (1.96 mg) | Low 14 μl (0.14 mg) | High 4.5 ml | 20 μl | Low 10 | 0.452 ml |

Each experimental design matrix should be completed as quickly as possible in order to minimize sample age, preferably within about ½ hour. The blood sample should be at least 30 minutes old prior to starting and should also be less than 24 hours old.

After completing the matrix experiments, the histograms are analyzed visually. The best histograms in terms of which blood cell subpopulation separation are chosen and the data recorded (i.e., %A, %B, initial diluent (ml) and time (sec.). The selected data points are then utilized as the starting criteria for the next matrix. This procedure is repeated until the data is visually optimized.

After the data has been visually optimized, the final matrix is used to determine correlation of a manual count with an automated count for each run. At least 35 different blood specimens from the same animal species should be used at this point in the procedure. The differential analysis of each matrix box for all 35 specimens is then compared to the manual differential of white blood cell subpopulations.

An example of the final matrix is set forth in Table 4 below.

TABLE 4

| | | (lymphocytes) | | | | | | |
|---|---|---|---|---|---|---|---|---|
| | | Run No. | | | | | | |
| Specimen | Manual | 12 | 17 | 3 | ... | 11 | 7 | 14 |
| 1 | 28 | 46 | 26 | 38 | | 36 | 20 | 19 |
| 2 | 44 | 64 | 43 | 53 | | 54 | 34 | 30 |
| 3 | 10 | 43 | 12 | 21 | | 20 | 6 | 8 |
| 35 | 38 | 61 | 41 | 47 | | 45 | 33 | 29 |

Using the aforementioned illustrated experimental design, the reagent system of the present invention can be optimized for virtually any animal species.

From the above description it is apparent that the objects of the present invention have been achieved. While only certain embodiments have been set forth, alternative embodiments and various modifications will be apparent from the above description to those skilled in the art. These and other alternatives are considered equivalents and within the spirit and scope of the present invention.

Having described the invention, what is claimed is:

1. A reagent kit for use in the automated or semi-automated differential analysis of white blood cells comprising:
   (a) a predetermined volume of a lytic reagent composition, for stromatolyzing red blood cells and selectively shrinking white blood cells into at least three subpopulations; and
   (b) an isotonic blood diluent, wherein the lytic reagent composition comprises:
   an aqueous solution of active lytic reagents selected from the group consisting of
   (a) an admixture of at least one different group (A) aliphatic quaternary ammonium compound with at least one group (B) aromatic, heterocyclic or zwitterionic quaternary ammonium compound;
   (b) an admixture of at least one group (A) aliphatic quaternary ammonium compounds with at least one group (C) heterocyclic quaternary ammonium compound; and
   (c) an admixture of at least one group (C) heterocyclic quaternary ammonium compound with at least one group (B) aromatic, heterocyclic or zwitterionic quaternary ammonium compound; wherein
   the group (A) quaternary ammonium compound is represented by the formula:

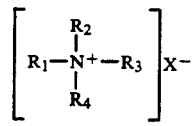

wherein $R_1$ is a long chain alkyl group containing from 10 to 20 carbon atoms, $R_2$, $R_3$ and $R_4$ are short chain alkyl groups containing from 1 to 6 carbon atoms, and X is an ion selected from the group consisting of halide, sulfate, phosphate, nitrate ions, and

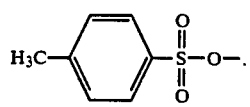

the group (B) quaternary ammonium compound is represented by the formula:

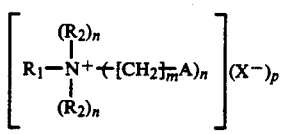

wherein $R_1$ is a long chain alkyl group comprising from 8 to 20 carbon atoms, $R_2$ is an alkyl group containing 1 to 6 carbon atoms, m is an integer from 1 to 4, A is a radical selected from the group consisting of:

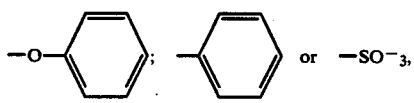

n is an integer from 0 to 1, such that when n=0, the remaining (N) bonds form part of a heterocyclic ring, X is an ion selected from the group consisting of halide, phosphate, sulfate and nitrate ions and p is an integer from 0 to 1;

the group (C) quaternary ammonium compound is represented by the formula

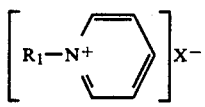

wherein $R_1$ is a long chain alkyl radical comprising from 10 to 20 carbon atoms, and X is an ion selected from the group consisting of halide, sulfate, phosphate and nitrate ions;

wherein the individual quaternary ammonium compound components of said lytic reagent are present in a ratio and quantity sufficient to effect at least a three component differential separation of white blood cells;

and the isotonic blood diluent has a predetermined pH and osmolality.

2. A reagent kit according to claim 1, wherein the lytic reagent composition component further comprises a chromagen forming reagent.

3. A reagent kit according to claim 2, wherein the chromagen forming reagent is potassium cyanide.

4. A reagent kit according to claim 1, where the isotonic blood diluent comprises at least one organic buffer, and a cell membrane stabilizing and antimicrobial agent.

5. A reagent kit according to claim 4, wherein the buffer comprises at least one member selected from the group consisting of ADA, MOPS, PIPES, HEPES, BES, BIS-TRIS, TES, TAPSO, MES, DIPSO, MOPSO, TRIS and ACES and the membrane stabilizing and antimicrobial agent is a monoaldehyde.

6. A reagent kit according to claim 4, wherein the lytic reagent composition is formulated for the differential analysis of a whole blood sample of human blood.

7. A reagent kit according to claim 4, wherein the lytic reagent composition is formulated for the differential analysis of a whole blood sample of a non-human animal.

8. A reagent kit according to claim 4, wherein the reagent composition comprises an aqueous solution of active lytic reagents comprising at least one aliphatic quaternary compound from group (A) and at least one aromatic, heterocyclic or zwitterionic quaternary ammonium compound from group (B), wherein the ratio of the amount of the group (A) compound to the amount of the group (B) compound in the aqueous solution ranges from about 5:1 to about 75:1.

9. A reagent kit according to claim 8, wherein the aliphatic quaternary compound of group (A) is selected from the group consisting of dodecyl trimethyl ammonium halide and dodecylethyl dimethyl ammonium halide and the group (B) quaternary ammonium compound is 1-dodecyldimethyl(2-phenoxyethyl) ammonium bromide.

10. A reagent kit according to claim 4, wherein the reagent composition comprises an aqueous solution of active lytic reagents comprising at least one aliphatic quaternary ammonium compound from group (A) and at least one heterocyclic quaternary ammonium compound from group (C) wherein the ratio of the amount of (A) to the amount of (C) in the aqueous solution ranges from about 0.01:1 to about 99:1.

11. A lytic reagent composition according to claim 10, wherein the aliphatic quaternary compound of group (A) is selected from the group consisting of dodecyltrimethyl halide and dodecylethyl dimethyl ammonium halide and the group (C) heterocyclic quaternary ammonium compound is 1-dodecyl pyridinium chloride.

12. A reagent kit according to claim 4, wherein the reagent composition comprises an aqueous solution of active lytic reagents comprising at least one aliphatic quaternary ammonium compound from group (C) and at least one aromatic, heterocyclic or zwitterionic quaternary ammonium compound from group (B), wherein the ratio of the amount of the group (C) compound to the amount of the group (B) compound in the aqueous solution ranges from about 5:1 to about 75:1.

13. A reagent kit according to claim 12, wherein the heterocyclic quaternary compound of group (C) is 1-dodecylpyridinium chloride and the group (B) compound is a benzyldimethyltetradecyl ammonium halide.

14. A lytic reagent composition for the automated differential analysis of white blood cells, comprising:
an aqueous solution of active lytic reagents selected from the group consisting of
(a) an admixture of at least one different group (A) aliphatic quaternary ammonium compound with at least one group (B) aromatic, heterocyclic or zwitterionic quaternary ammonium compound;
(b) an admixture of at least one group (A) aliphatic quaternary ammonium compounds with at least one group (C) heterocyclic quaternary ammonium compound; and
(c) an admixture of at least one group (C) heterocyclic quaternary ammonium compound with at least one different group (B) aromatic, heterocyclic or zwitterionic quaternary ammonium compound; wherein the group (A) quaternary ammonium compound is represented by the formula:

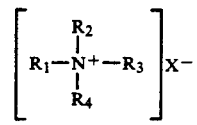

wherein $R_1$ is a long chain alkyl group containing from 10 to 20 carbon atoms, $R_2$, $R_3$ and $R_4$ are short chain alkyl groups containing from 1 to 6 carbon atoms, and X is an ion selected from the group consisting of halide, sulfate, phosphate, nitrate ions, and

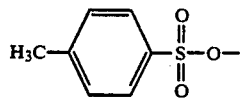

the group (B) quaternary ammonium compound is represented by the formula:

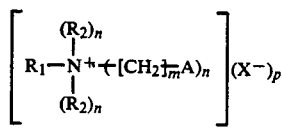

wherein $R_1$ is a long chain alkyl group comprising from 8 to 20 carbon atoms, $R_2$ is an alkyl group containing 1 to 6 carbon atoms, m is an integer from 1 to 4, A is a radical selected from the group consisting of:

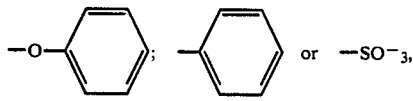

n is an integer from 0 to 1, such that when n=0, the remaining (N) bonds form part of a heterocyclic ring, X is an ion selected from the group consisting of halide, phosphate, sulfate and nitrate ions and p is an integer from 0 to 1;

the group (C) quaternary ammonium compound is represented by the formula

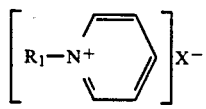

wherein $R_1$ is a long chain alkyl radical comprising from 10 to 20 carbon atoms, and X is an ion selected from the group consisting of halide, sulfate, phosphate and nitrate ions;

wherein the individual quaternary ammonium compound components of said lytic reagent are present in a ratio and quantity sufficient to effect at least a three component differential separation of white blood cells;

15. A lytic reagent composition according to claim 14, wherein the lytic reagent composition is formulated for the differential analysis of a whole blood sample of a non-human animal.

16. A lytic reagent composition according to claim 14, further comprising a chromagen forming reagent.

17. A lytic reagent composition according to claim 16, wherein the chromagen forming reagent is potassium cyanide.

18. A lytic reagent composition according to claim 14 wherein the lytic reagent composition is formulated for the differential analysis of a whole blood sample of a human blood.

19. A lytic reagent composition according to claim 18, wherein the reagent composition comprises an aqueous solution of active lytic reagents comprising at least one aliphatic quaternary compound from group (A) and at least one aromatic, heterocyclic or zwitterionic quaternary ammonium compound from group (B), wherein the ratio of the amount of the group (A) compound to the amount of the group (B) compound in the aqueous solution ranges from about 5:1 to about 75:1.

20. A lytic reagent composition according to claim 19, wherein the aliphatic quaternary compound of group (A) is selected from the group consisting of dodecyl trimethyl ammonium halide and dodecylethyl dimethyl ammonium halide and the group (B) quaternary ammonium compound is 1-dodecyldimethyl(2-phenoxyethyl) ammonium bromide.

21. A lytic reagent composition according to claim 18, wherein the reagent composition comprises an aqueous solution of active lytic reagents comprising at least one aliphatic quaternary ammonium compound from group (A) and at least one heterocyclic quaternary ammonium compound from group (C) wherein the ratio of the amount of (A) to the amount of (C) in the aqueous solution ranges from about 0.01:1 to about 99:1.

22. A lytic reagent composition according to claim 21, wherein the aliphatic quaternary compound of group (A) is selected from the group consisting of dodecyltrimethyl ammonium halide and dodecylethyl dimethyl ammonium halide and the group (C) heterocyclic quaternary ammonium compound is 1-dodecyl pyridinium halide.

23. A lytic reagent composition according to claim 18, wherein the reagent composition comprises an aqueous solution of active lytic reagents comprising at least one heterocyclic quaternary ammonium compound from group (C) and at least one aromatic, heterocyclic or zwitterionic quaternary ammonium compound from group (B), wherein the ratio of the amount of the group (C) compound to the amount of the group (B) compound in the aqueous solution ranges from about 5:1 to about 75:1.

24. A lytic reagent composition according to claim 23, wherein the heterocyclic quaternary ammonium compound of group (C) is 1-dodecylpyridinium chloride and the group (B) quaternary ammonium compound is a benzyldimethyltetradecyl ammonium halide.

25. A lytic reagent composition according to claim 14 in admixture with an isotonic blood diluent, said diluent having a predetermined pH and osmolality.

26. A lytic reagent composition according to claim 25, wherein the ratio of the isotonic diluent to the lytic reagent composition ranges from about 2:1 to about 250:1.

27. A lytic reagent composition according to claim 26, wherein the isotonic diluent comprises at least one organic buffer and a cell membrane stabilizing agent and antimicrobial agent.

28. A lytic reagent according to claim 27, wherein the buffer comprises at least one member selected from the group consisting of ADA, MOPS, PIPES, HEPES, BES, BIS-TRIS, TES, TAPSO, MES, DIPSO, MOPSO, TRIS and ACES.

29. A lytic reagent composition according to claim 28, wherein the buffer is ACES.

* * * * *

UNITED STATES PATENT AND TRADEMARK OFFICE
CERTIFICATE OF CORRECTION

PATENT NO. : 5,316,725
DATED : May 31, 1994
INVENTOR(S) : Edward L. Carver et al It is certified that error appears in the above-identified patent and that said Letters Patent is hereby corrected as shown below:

In Claim 1, column 20, line 44 of the Patent, after "one" and before "group", insert --different--.

Signed and Sealed this

Eleventh Day of October, 1994

Attest:

BRUCE LEHMAN

*Attesting Officer*     *Commissioner of Patents and Trademarks*